United States Patent [19]

Hofmeier et al.

[11] Patent Number: 4,596,649

[45] Date of Patent: Jun. 24, 1986

[54] MEASURING SYSTEM COMPRISING ION-SELECTIVE ELECTRODES

[75] Inventors: Gerhard Hofmeier, Hamburg; Wolfgang Tscheu, Henstedt-Ulzburg, both of Fed. Rep. of Germany

[73] Assignee: Eppendorf Gerätebau Netheler & Hinz GmbH, Fed. Rep. of Germany

[21] Appl. No.: 712,355

[22] Filed: Mar. 15, 1985

[30] Foreign Application Priority Data

Mar. 16, 1984 [DE] Fed. Rep. of Germany ....... 3409666

[51] Int. Cl.$^4$ ............................................. G01N 27/28
[52] U.S. Cl. ..................................... 204/411; 204/409
[58] Field of Search ....................... 204/411, 409, 412; 422/68, 81

[56] References Cited

U.S. PATENT DOCUMENTS

| | | | |
|---|---|---|---|
| 3,884,640 | 5/1975 | Lock et al. | 422/68 |
| 3,966,413 | 6/1976 | Marinenko | 204/411 X |
| 4,160,714 | 7/1979 | Andersen et al. | 204/411 |
| 4,206,027 | 6/1980 | Schindler et al. | 204/411 |
| 4,361,539 | 11/1982 | Weinberg et al. | 422/68 |
| 4,361,540 | 11/1982 | Weinberg et al. | 422/68 |
| 4,404,065 | 9/1983 | Matson | 204/411 X |
| 4,443,407 | 4/1984 | Weinberg et al. | 422/68 |

FOREIGN PATENT DOCUMENTS

2652370 5/1978 Fed. Rep. of Germany ........ 422/68

Primary Examiner—G. L. Kaplan
Attorney, Agent, or Firm—Toren, McGeady, Stanger, Goldberg & Kiel

[57] ABSTRACT

A measuring system comprises ion-selective electrodes adjoining a measuring passage, which has an inlet and an outlet. The measuring passage has bends, which are adjoined by the sensing electrodes, which are flush with the boundary surface of that measuring passage. Said bends extend also before and behind each electrode. The sensing electrodes are provided at the outside surface of each bend so that they will be effectively rinsed and errors due to entrained impurities will be avoided. The measuring passage is suitably substantially circular but has entrance and exit portions offset from the circular line. The electrodes are provided on the outside particularly in a star-shaped array. The measuring system is provided with a shield consisting of a closed, electrically conducting covering, which preferably consists of a metallic cover. Contact and contact pressure springs are subjected to a uniform stress because the cover is mounted with play by means of a hinge so that self-alignment will be effected.

19 Claims, 7 Drawing Figures

MEASURING SYSTEM COMPRISING ION-SELECTIVE ELECTRODES

BACKGROUND OF THE INVENTION

1. Field of the Invention

This invention relates to a measuring system comprising ion-selective sensing electrodes adjoining a measuring passage having an inlet and an outlet, which electrodes are provided at a boundary surface of that measuring passage and are flush with that surface.

Within the scope of the invention, contact and pressure contact pressure springs may be associated with all said electrodes.

Within the scope of the invention the measuring passage may extend in known manner through transparent components. This will facilitate the supervision.

2. Description of the Prior Art

A measuring system which is of the kind described first hereinbefore and comprises straight measuring passage sections is known from Published German Application Nos. 26 52 370 and 27 26 772. In said systems the measuring electrodes are screwed into their installed position. The screwed connection has the disadvantage that a uniform positioning of the electrodes relative to the measuring passage is not ensured because different tightening forces may inadvertently be exerted or because impurities which are present may have the result that the final position is not the same for all electrodes. Besides, some ion-selective electrodes are provided on their sensing surface with a protecting membrane, which may be destroyed by the sealing ring which surrounds the actual electrode surface and is clamped as the sensing electrode is screwed into position. Such destruction may result in non-uniform measurements and will reduce the utility of the system in a manner which is not readily detectable.

The measuring passage of the known system includes measuring chambers, which consist of respective recesses, which have a somewhat lower depth than the adjoining portions of the passage. That design results in a retention of the liquid to be measured in said recesses and in an irregular flow and a deflection of said liquid and may result in a separation of the flow from the sensing electrodes.

In accordance with Published German Application No. 31 16 321, hemispherical measuring chambers are provided between straight measuring passages extending along a zig-zag course. The electrodes protrude into said measuring chambers and are contacted in an undefined manner by the flowing liquid or the liquid flowing through the measuring passages may separate from the electrodes where said passages join said chambers. Even when the liquid is stagnant during the measurement, that known system will not ensure a uniform wetting of the electrodes and errors due to entrained impurities may also occur because there is no smooth flow but a retention and turbulence and there are dead spaces so that a reliable flow in contact with the electrodes and in any case a uniform flow in contact with the electrodes is not ensured. In the known system the electrodes are electrically connected to cables. This has the disadvantage that electrical interference may be detected by the sensor, i.e., the electrode, interference may be detected by the sensor, i.e., the electrode, and may be transmitted to the signal-processing circuitry.

In accordance with Published German Application No. 31 15 321, the cell which is flowed through consists of transparent material and the electrodes are axially forced against a seal by a compression spring and are thus held in position. Whereas that resilient contact pressure affords an advantage, that arrangement may not ensure an even flow in contact with the electrodes particularly when the electrode is forced against an elastic seal in an arrangement comprising straight measuring passage sections.

SUMMARY OF THE INVENTION

It is an object of the invention to provide a measuring system which is of the kind described first hereinbefore and which is so designed that particularly for use with quantities of liquid of an order of microliters it will be ensured that residues of a sample liquid will be rinsed from the sensing electrodes and the next succeeding sample will reliably flow in contact with the electrode surfaces. Electrical interference in the signal-processing circuitry and along the line leading to such circuitry are to be avoided.

Electrical interference includes such interference occurring along the transmission line, e.g., capacitive interference resulting from movements of the known cables, as well as external other influences.

The object stated above is accomplished in accordance with the invention in that the measuring passage has a bend at and before and behind each electrode and each electrode is provided at that boundary surface which is disposed on the outside of the associated bend.

This arrangement ensures that the sample liquid will flow in contact with the electrode surface and that a satisfactory rinsing particularly of the electrode surface will be effected between the measuring of different samples. A highly accurate measurement is ensured because the entire sample liquid is conducted to the measuring electrodes without and errors which might be due to entrained impurities. This is accomplished by the special rinsing effect, which is due to the bends of the measuring passage and the specific arrangement of the sensing electrodes.

The flow of the sample liquid in the curved measuring passage ensures that said liquid will contact and wet the electrode surfaces even if the sample liquid is stagnant at the time of the measurement. The supply of the sample liquid and the remaining effective atmospheric pressure will ensure that an unfavorable boundary layer flow will be avoided and that the sample liquid will be conducted in a favorable manner past the electrodes. In conjunction with the rinsing, any clogging, incrustation and residues will be avoided, particularly on the electrode surfaces.

In accordance with another aspect, which may be combined with the above arrangement, the system comprises a shield consisting of an electrically conducting closed covering, particularly of a metallic cover. The electrically conducting covering may consist, e.g., of conducting plastic or of a metal wire mesh.

If the measuring system is accommodated in a housing, that housing will preferably comprise a base and a shield, which may particularly consist of a cover. Special advantages will be afforded if the features are used in a compact arrangement.

An embodiment in which contact and contact pressure springs are associated with all electrodes may be provided with a shield and may be designed to ensure a uniform function of all electrodes. It will be particularly desirable to provide the system in a housing having a cover which is connected to the base by a hinge, which provides for a play so that the cover will be guided and will be self-aligning under the action of reaction forces exerted by contact and contact pressure springs, which are provided, and said cover will be yieldably mounted for self-alignment. Particularly in conjunction with the specific arrangement of the electrodes, a uniform contact pressure is obtained at the bend of the measuring passage.

In a preferred embodiment, such an arrangement will be further improved if components of a signal-processing circuitry including transducers and amplifiers are accommodated in the cover and an integral contact pin providing a mechanically rigid electrical connection extends between the contact springs and the components of said circuitry. Losses which could be caused by flexible connections will thus be avoided and the electrically conducting path is constituted by rigid means. At high-resistance components, rigid contacts are preferred in order to preclude capacitive disturbances caused by mechanical movements.

The combination of said features results in a measuring system which has optimum measuring capabilities.

In a suitable embodiment the curved measuring passage consists of a plurality of sections, which may be curved in mutually opposite senses and each of which contains an electrode. A meandering measuring passage is preferred. In another desirable embodiment the measuring passage extends along a helix and the electrodes are arranged on different levels.

In such an arrangement the electrodes are accommodated in a very small space but on different levels so that more space for means for mounting the electrodes is available on the outside whereas the electrodes are rather closely spaced apart at the measuring passage. Such close spacing is desirable because it permits the measurement of small-volume samples.

In a special embodiment which is desirable also from that aspect the measuring passage is substantially circular but has inlet and outlet portions which are offset from the circular line and the electrodes are disposed on the outside of said passage, particularly in a star-shaped array. In that case the electrodes can be provided in the form of a disc-like star-shaped array so that a large space for access to the electrodes is available on the outside of the measuring passage. This is also ensured by the embodiment described in the preceding paragraph and affords special advantages if the measuring passage is substantially circular for instance, substantially C-shaped.

The electrodes are preferably plugged into radial openings and a concentric circular series of contact and contact pressure springs is provided for all electrodes. Such contact and contact pressure springs used in combination with the star-shaped electrode array will have a uniform action so that if the electrodes are surrounded by sealing means an absolutely uniform contact pressure will be ensured even. In that case, mutually corresponding, radially symmetrical contact pressure-applying and adjusting means are provided.

In a particularly preferred embodiment the function of the circular series of spring is performed and other advantages are provided by the cooperation with the above-mentioned cover. That cover permits the housing to be closed when the system is in an operative condition and ensures also a uniform contact pressure at all electrodes.

In a preferred embodiment the substantially circular housing member which defines the measuring passage contains spring-loaded catches, which are parallel to the openings receiving the electrodes and serve to latch the electrodes. For that purpose said catches enter detent openings, which are formed in the electrodes and are longer than the surface in contact with the corresponding catch. Such catches provide for a certain play so that the radial symmetrical contact pressure will not be adversely affected.

It has been stated above that transparent components have been used in a known arrangement. Within the scope of the invention the use of such transparent components in combination with the concentric, virtually star-shaped array of the sensing electrodes permits of a particularly desirable design in which the circular housing member contains a centrically arranged, transparent cylinder, which defines the measuring passage and is provided with an open-topped recess permitting of a visual inspection of the measuring passage. The recess is suitably conical with side faces tapering at an angle of about 45°. This arrangement will permit a particularly favorable inspection throughout the circumference.

It will be understood that the measuring passage is suitably adjoined also by a reference electrode, which precedes the outlet of said passage and is suitably arranged within the cover, and that a special inlet for a rinsing liquid is suitably provided in the housing member within the cover and disposed between the reference electrode and the series of sensing electrodes.

The above-mentioned reference to mechanically rigid means consisting of an integral contact pin for effecting an electrical connection in combination with the shield may be used in a desirable embodiment, in which the mechanically rigid connecting means include a protective resistor, which has a current-limiting function and ensures that no malfunction will be caused by a direct touch of the contacts by an operator when the cover is open.

The curved measuring passage mentioned above is constituted in one embodiment of a groove in a measuring passage cylinder, which is preferably transparent. In accordance with a further desirable feature, only part of that curved measuring passage is formed in the measuring passage cylinder and another part of said passage is arranged in cross-section in mirror symmetry to the first mentioned part and formed in a cylindrical sleeve, which surrounds the measuring passage cylinder. In such an arrangement, each of said parts of the measuring passage may consist of a groove having rounded corners in cross-section. This design will result in an improved adaptation of the measuring passage to the conditions of flow and particularly that passage-defining surface on which the sensing surface of the sensing electrodes is provided may have a shape which is desirable from the aspect of flow dynamics. The measuring passage cylinder and/or the cylindrical sleeve may be formed with an opening through which a projection of the sensing electrode may be inserted and said opening may have a cross-sectional dimension which exceeds the dimension of the measuring passage at right angles to the axis of the projection. In such an arrangement the sealing ring provided on the outise of the projection constitutes an elastic support, which will be clamped between the sensing electrode and a shoulder surrounding the projection of the sensing electrode when its forward end face bears on a shoulder which surrounds a mouth at which the opening adjoins the measuring passage. This arrangement will facilitate the manufacture and will not adversely affect the supervision.

DETAILED DESCRIPTION OF THE PREFERRED EMBODIMENTS

Figure 1:
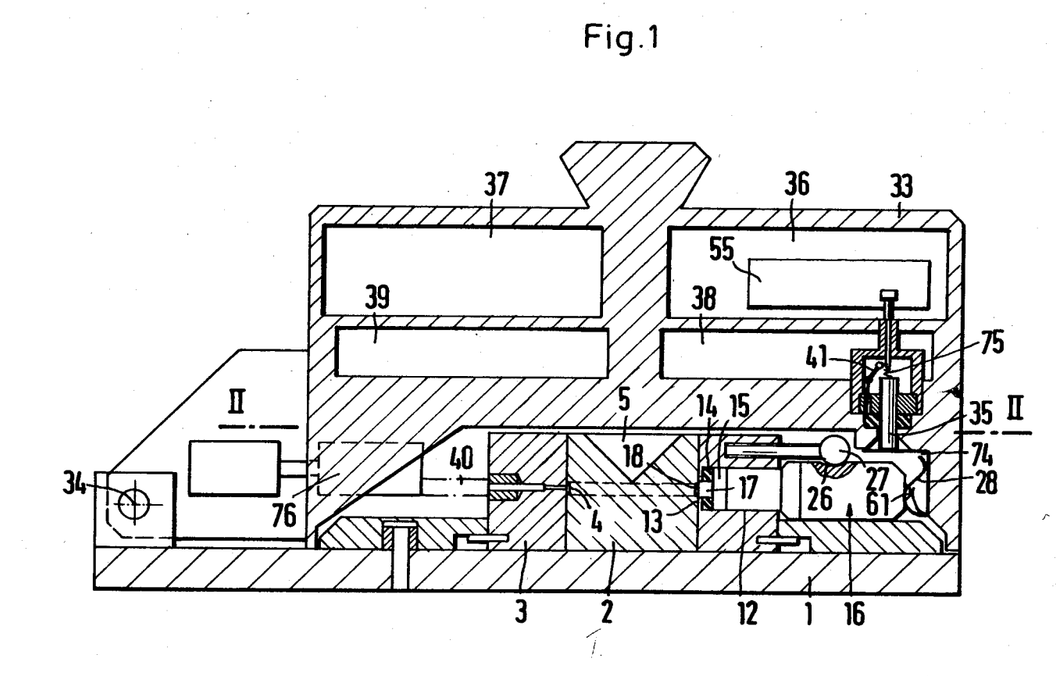
FIG. 1 is a diagrammatic vertical longitudinal sectional view showing a measuring system.
Figure 2:
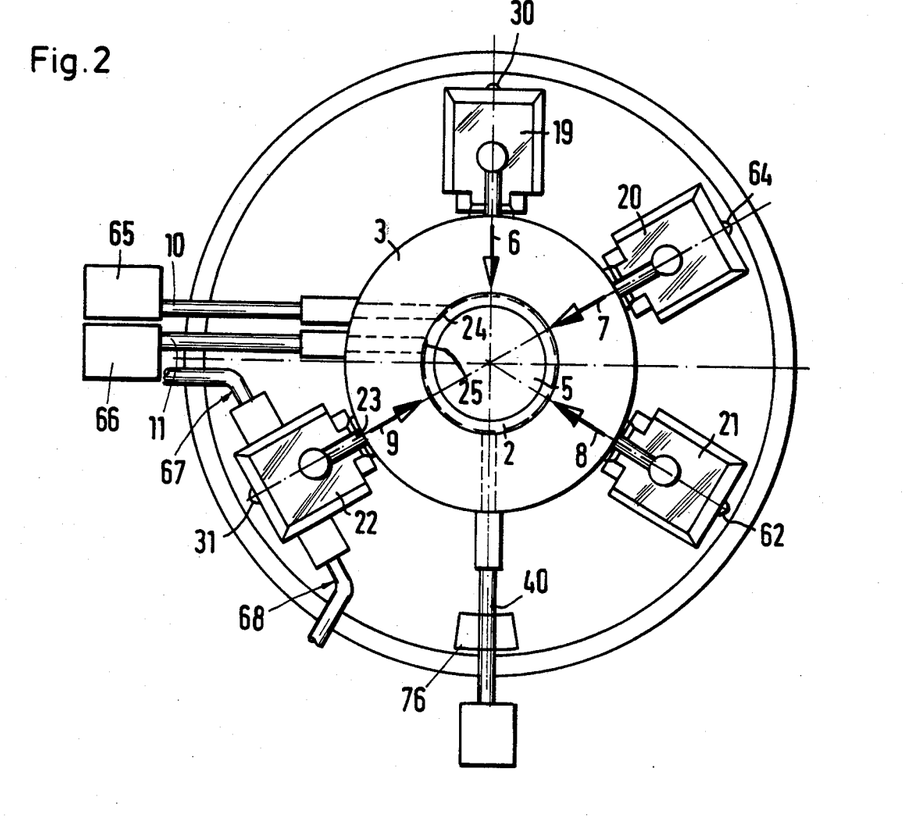
FIG. 2 is a top plan taken on line II—II in FIG. 1 when the cover has been removed.
Figure 3:
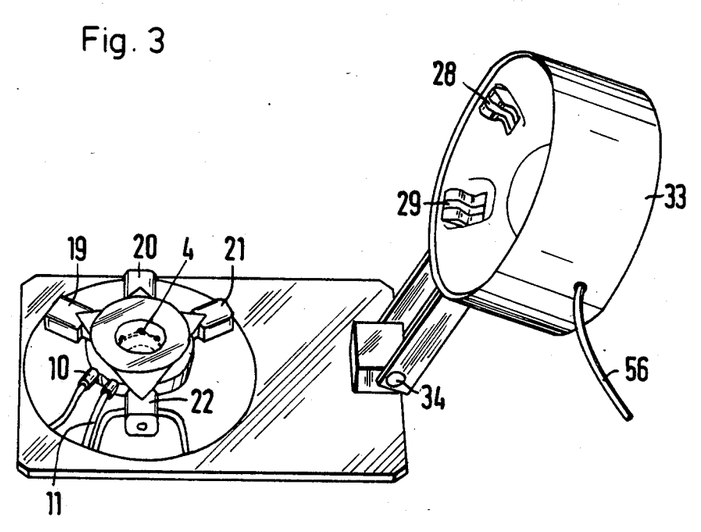
FIG. 3 is a perspective view showing the system of FIG. 1.

A preferred embodiment is shown in FIGS. 1 to 3 and comprises a base 1, a measuring passage cylinder 2 made of a transparent material, such as polymethyl methycrylate, and mounted on the base 1. The cylinder 2 is surrounded by a cylindrical sleeve 3 of plastic. Approximately in the middle of its height, the measuring passage cylinder 2 is formed on the outside with a peripheral groove, which has rounded corners in cross-section and constitutes a measuring passage 4 or, in the embodiment shown in FIG. 6, constitutes a portion of a measuring passage. In the transparent measuring passage cylinder 2 that peripheral groove can be inspected from above through a recess 5. The inspection is facilitated in that the recess 5 is conical and has side faces inclined at an angle of 45°. The rounded corners will promote the adaptation to the natural flow pattern.

The cylindrical sleeve 3 is in snug contact with the measuring passage cylinder 2 so that an escape of liquid at the interface will be prevented. The cylindrical sleeve 3 has radial openings 6 to 9 and is provided with inlet and outlet pipes 10, 11 serving for the supply and withdrawal of a sample liquid. The sample liquids consist of serums, which may be diluted or concentrated, or of plasma, whole blood, or body liquors. Such samples must be analyzed in very small quantities and within a very short flow path and no errors due to entrained impurities must occur in the measurement of consecutive samples of such liquids. The samples have a volume of an order of about 30 micorliters.

In accordance with FIG. 2 the inlet and outlet pipes 10, 11 are provided with devides 65, 66, which may contain valves or a reservoir as well as pumping means so that the pipes 10, 11 may be associated with inlet and outlet devices.

The openings 6 to 9 provided in the cylindrical sleeve 3 constitute mounts for sensing electrodes and as is apparent from FIG. 1 each of the openings 6 to 9 comprises a cylindrical cavity 12 and a constricted passage 13, and a sealing ring 14 is accommodated in the cylindrical cavity 12 near the constricted passage 13. The sensing electrode generally designated 16 has a collar 15, which is urged against the sealing ring 14. Each sensing electrode 16 constitutes an assembly, which in the usual manner comprises a guide housing and conducting elements. Such an electrode or electrode assembly comprises a projection 17, which is so matched to the thickness of the sealing ring 14 that the forward end face 18 of the projection 17 is flush with the boundary surface of the measuring passage 4. A modification adopted to ensure an exact positioning of the forward end face will be described hereinafter with reference to FIG. 6.

In an arrangement comprising, e.g., three sensing electrodes 19 to 21 it is difficult to effect a uniform positioning of the electrode faces 18. Besides, a reference electrode 22, which corresponds to a sensing electrode 23, extends to the measuring passage and in the direction of flow precedes the outlet pipe 11 or the mouth 25 of said pipe merging into the end of the measuring passage 4. The cover accommodates inlet and outlet pipes 67, 68 associated with the reference electrode 22. The measuring passage 4 is interrupted between the mouth 24 of the inlet pipe 10 and the above-mentioned mouth 25.

As is apparent from FIG. 1, each of the sensing electrodes 19 to 22 and the reference electrode 22 has at its top a detent recess 26, which receives a latching element consisting of a catch 27, which in the present embodiment consists of a ball head carried by a resilient arm, which is mounted on the cylindrical sleeve. That catch 27 ensures that the electrodes will assume such a position that under the action of an aligning and contact pressure-applying element, such as a ring, they will be reliably engaged by contact pressure-applying means carried by such contact pressure-applying element. Such contact pressure-applying means may consist of springs 28, 29. Such a contact pressure-applying device may consist in the preferred embodiment of a cover, which will be described hereinafter. In the radial direction with respect to a center line of the assembly or in the direction of the longitudinal axis of the sensing electrode the dimension of the recess 26 exceeds the length in which the recess 26 is in contact with the catch 27.

All electrodes are subjected to contact pressure from the outside by springs, one of which is designated 28 in FIG. 1. Such springs bear on the electrodes at contacts 30, 31, 62, 64 (FIG. 2) of the electrodes. The springs are spaced around the periphery of the system, i.e., around its center line 32. The provision of cooperating yieldable elements ensures a concentric arrangement as well as a uniform contact pressure between the collars 15 of all electrodes 16 and the sealing rings 14 provided on the outside of the measuring passage 4 so that equal forces will be exerted on all sealing rings 14. Two contact springs 28, 29 are shown in the cover 33 in FIG. 3 and are equally spaced from the center line.

That advantage will be afforded in a particularly desirable manner if all contact pressure springs 28, 29 are carried by a ring 69, which is particularly provided within a cover 33, which is hinged to the base 1 by means of a hinge 34.

Figure 7:
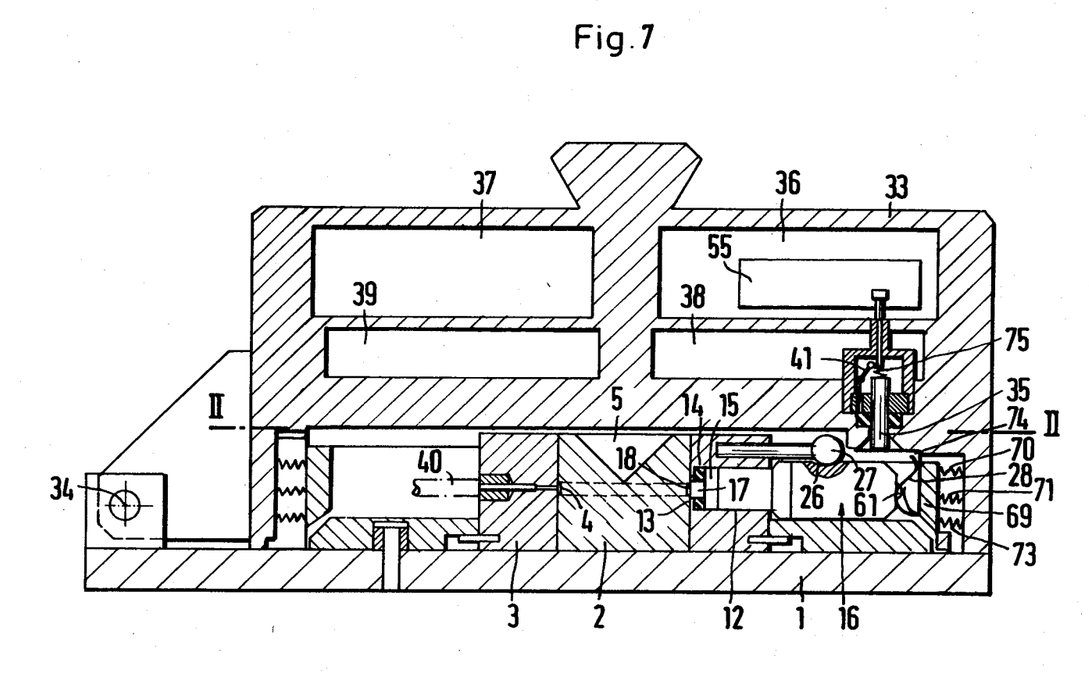
FIG. 7 is a diagrammatic vertical longitudinal sectional view that is similar to FIG. 1 and shows modified means for centering the electrodes.

The ring 69 is floatingly mounted in the cover 33. For this purpose the ring 69 is supported along its periphery by means of a spring ring or a circular series of springs or by means of spring sets spaced around the periphery. In the present embodiment, each of said spring sets comprises three springs 70, 71, 73. It is apparent that in that embodiment the contact pressure-applying means, particularly the springs 28, 29 shown in FIG. 3, are mounted on such ring 69 and that said spring are also in contact with respective contacts 74, which will be insulated from the cover if the latter consists of metal. Said contacts are connected to respective contact pins 35. Particularly if the ring 69 shown in FIG. 7 is provided, the contact 74 will be in sliding contact with the contact pin 35.

In the embodiment shown in FIG. 1 the hinge 34 associated with the cover provides for a play in any direction to such an extent that an alignment is effected under the reaction of the spring 28 or springs 28, 29 so as to ensure a uniform contact pressure at the electrodes.

It is apparent from FIG. 1 that each of the springs 28, 29 is connected to a contact pin 35, which is directly connected to circuit components 55, which are accommodated in the compartments 36, 37 and possibly also in compartments 38, 39 of the cover. A spring 75, urges the contact pin 35 against the contact 74. The circuit components 55 comprise amplifiers and/or transducers, which are directly connected so that they will not be affected by mechanical shakes which might be caused by movable contacts. In this case there is a rigid connection. The electrically conducting path includes a protective resistance 41, which prevents a malfunction caused by an operator touching the live circuitry when the cover is open.

The measuring passage 4 can be supervised when the cover has been opened. It is apparent from FIG. 1 that an additional inlet 40 is provided for receiving a rinsing liquid from a hose connected to a directional valve. That pipe 40 may be provided in the cover and associated with an inlet assembly 76, which includes pressure relief valves. Other controls and pumping means and reservoirs associated with the directional valve may be provided outside the cover.

FIGS. 1 to 3 show the preferred embodiment in which the measuring passage 4 is almost circular and has a C-shaped configuration. It is apparent that the electrodes constitute a star-shaped array so that there is adequate space for the connections at the outer ends of the electrodes whereas the measuring passage is extremely small.

Figure 4:
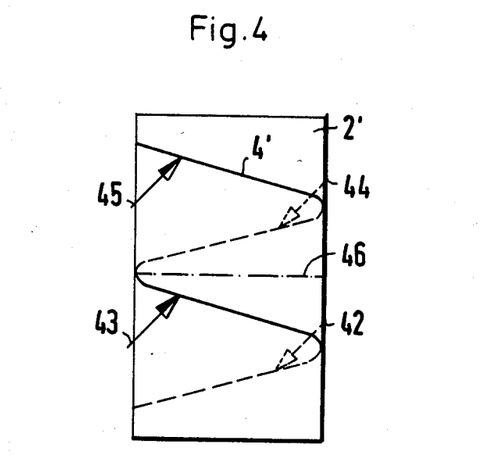
FIG. 4 is a diagrammatic side elevation showing part of another embodiment.

FIG. 4 shows only one measuring passage cylinder 2′, which defines a helical measuring passage 4′, and also shows electrodes spaced around the periphery as is indicated by arrows 42 to 45 and are disposed on different levels. Each of said electrodes extends inwardly to and adjoins the measuring passage. Such measuring passage cylinder is subdivided along a parting line 46 into two disc-like sections so that any desired number of sensing electrodes may be provided in a star-shaped array with respect to a center line and said electrodes may be subjected to a uniform contact pressure by at least one circular series of springs.

In such an arrangement a rinsing liquid and a sample liquid which are supplied and withdrawn by pressure and, if desired, a vacuum, will flow under the resulting forces on the outside surface of the measuring passage, i.e., on that surface where the sensing electrode faces are provided, so that said faces will be intensely cleaned by the rinsing liquid flowing in contact with said surfaces and will be intensely wetted by the sample liquid during the measurement, when the sample liquid is stagnant. Any cavitation can occur in such a small measuring passage only on the boundary surface which is opposite to the sensing electrodes so that such cavitation will not exert an influence.

Figure 5:
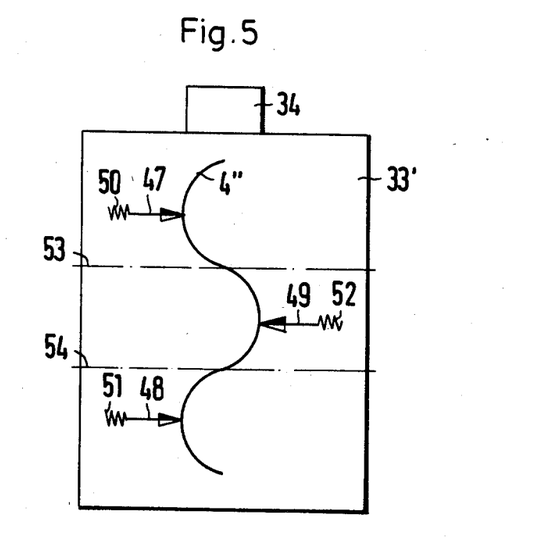
FIG. 5 is a diagrammatic side elevation showing the course of a measuring passage for an explanation of a different embodiment.

In the embodiment shown in FIG. 5 the measuring passage 4″ has a meandering shape and a sensing electrode 47 and 48 or 49 is provided on the outside of each bend. Such sensing electrodes may also be subjected to uniform contact pressures by springs 50 to 52 mounted in a common cover 33′, which is mounted by means of a hinge 34′ providing for a play, just as has been described hereinbefore. The inlets and outlets are not shown in FIG. 5 but their arrangement will be apparent from the description given hereinbefore. The embodiment shown in FIG. 5 that the measuring passage can be divided at the parting lines 53, 54 into sections, each of which may or may not be provided with electrodes so that the number of sensing cells can be altered whereas the advantages are preserved.

As is shown in FIG. 3, a power supply cable 56 extends in the cover 33.

Figure 6:
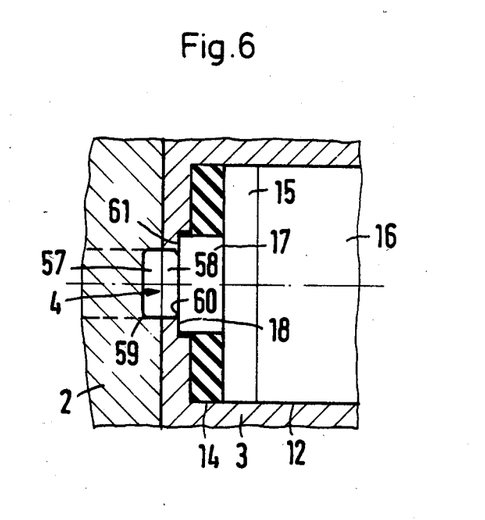
FIG. 6 is a fragmentary view showing a portion of FIG. 1 and serves for an explanation of a special embodiment of the measuring passage and of an associated sensing electrode.

FIG. 6 is an enlarged view showing a portion of FIG. 1 with the projection 17 and the forward end face 18 of the sensing electrode, the sealing ring 14 and the associated portion of the measuring passage 4. In this embodiment a different design of the measuring passage 4 is combined with a special arrangement for the contact of the sensing electrode.

FIG. 6 shows a portion of the measuring passage cylinder 2 and the adjoining portion of the cylindrical sleeve 3. In this embodiment the measuring passage consists of two grooves 57, 58, which are arranged in mirror symmetry in cross-section and communicate with each other. Said grooves are respectively formed in the measuring passage cylinder 2 and in the cylindrical sleeve 3 and in cross-section have rounded corners such as 59, 60. The height of that measuring passage is smaller than the diameter of the projection 17 of the sensing electrode 16. The forward end face 18 of the projection 17 directly adjoins the boundary of the measuring passage 4, i.e., the boundary of the groove 58, which is open to the sensing electrode 16 near the rounded corners 60. It is apparent that the cylindrical cavity communicates through the constricted passage 13 with the measuring passage 4 and that the sealing ring 15 ensures a reliable contact between the shoulder 61 of the cylindrical sleeve 3 and the projection 17 of the sensing electrode and between the latter and the sealing ring 14 around the constricted passage 13.

In that embodiment the thickness of the sealing ring 14 is so matched to the length of the projection 17 that the sealing ring 14 will be compressed when the collar 15 of the sensing electrode bears on the sealing ring 14 and the forward end face 18 engages the shoulder 61 and adjoins the boundary surface of the measuring passage 4.

This design will result in particularly favorable conditions of flow.

It will be understood that the measuring passage 4 shown in FIG. 1 may also have rounded corners in cross-section, like the rounded corners 59 of the groove 57, and it is also apparent from FIG. 1 that the height of the measuring passage 4 is smaller than the diameter of the projection 17. The provision of the shoulder 61 adjoining the measuring passage 4 in the cylindrical sleeve 3, as shown in FIG. 6, affords the advantage that all elements supporting the sensing electrode 16 are disposed in the same component. The measuring passage is tight owing to the snug contact between the measuring passage cylinder 2 and the cylindrical sleeve 3. The measuring passage 4 is small in cross-section and in an illustrative embodiment has a hight of 2 mm and a depth, viewed from the electrode, of 0.3 mm.

Reference to U.S. Pat. No. 4,366,040 is made as regards the electrodes and the measuring technology.

We claim:

1. In a measuring system comprising
passage-defining means defining a measuring passage having an entrance portion and an exit portion,
a plurality of ion-selective sensing electrodes adjoining said measuring passage between said entrance and exit portions and spaced apart along said measuring passage and adapted to examine fluid samples flowing through said measuring passage from said entrance portion to said exit portion and contacting said sensing electrodes,
an inlet device connected to said entrance portion, and an outlet device connected to said exit portion, the improvement comprising that
said measuring passage comprises a plurality of bends, each of which is adjoined by one of said sensing electrodes and has curved portions respectively preceding and succeeding said sensing electrode in the direction from said entrance portion to said exit portion, wherein
each of said sensing electrodes adjoins said bend on the outside thereof, and
electrode-mounting means are provided and carry said sensing electrodes,
a shield consisng of an electrically conducting, closed cover is provided,
a sub-assembly comprising said passage-defining means and said sensing means is provided, and
said cover is removably connected to said sub-assembly and provides a protective screen.

2. The improvement set forth in claim 1, wherein
a cover (33) is yieldably mounted by a hinge (34), said hinge provides a play for said cover,
said sensing electrodes are provided with contacts (30, 31; 62, 64),
said cover (33) contains contact and contact pressure springs (28, 29),
the arrangement is such that when the cover is closed the contact and contact pressure springs (28, 29) engage said contacts (30, 31; 62, 64) in such a manner as to constrain and align said cover (33) under the action of the reaction forces of said springs and to effect a uniform mechanical loading of said contacts of all said electrodes.

3. The improvement set forth in claim 2, wherein
said cover (33) contains components of signal-processing circuitry comprising transducers and amplifiers,
contact and contact pressure springs (28, 29) biasing said electrodes are provided,
mechanically rigid means are provided, which electrically connect said springs to and said signal-processing circuit and comprise an integral contact pin (35), which is yieldably mounted and adapted to be positioned by the contact and contact pressure springs (28, 29).

4. The improvement set forth in claim 3, wherein said mechanically rigid means comprise a protective resistor (41), which is connected in circuit between said springs and said evaluating circuit and is adapted to protect said evaluating circuit from the influence of a touch by a human being when said cover (33) is open.

5. The improvement set forth in claim 1, wherein consecutive ones of said bends are curved in mutually opposite senses.

6. The improvement set forth in claim 1, wherein said passage-defining means comprise a plurality of detachably interconnected sections, each of which defines one of said bends and contains one of said sensing electrodes.

7. A measuring system comprising, in combination
a base,
a measuring passage cylinder, which is mounted on said base and defines a measuring passage formed with a plurality of bends,
a cylindrical sleeve, which surrounds said measuring passage cylinder and is formed with radial through openings,
ion-selective sensing electrode means extending in said opening and adjoining said measuring passage,
an inlet device and an outlet device extending through said cylindrical sleeve and communicating with said measuring passage, and
a shield consisting of an electrically conducting, closed cover, which is removably mounted on said base and consists of a protective screen.

8. A measuring system as claimed in claim 7, wherein said cover (33) is hinged to said base (1) and covers the entire base as well as said measuring passage cylinder (2), said cylindrical sleeve (3), and mounting means carrying said electrode means.

9. A measuring system as claimed in claim 7, wherein said measuring passage (4) comprises two portions, which communicate with each other and are respectively formed in said measuring passage cylinder (2) and in said cylindrical sleeve (3) and are arranged in mirror symmetry in cross-section and are constituted by respective grooves (57, 58) having rounded corners in cross-section.

10. A measuring system as claimed in claim 9, wherein
each of said openings has a mouth adjoining said measuring passage, an outer cavity, and a constricted passage extending from said outer portion to said mouth,
said constricted passage has at right angles to the longitudinal direction of said measuring passage (4) a cross-sectional dimension which is larger than the corresponding dimension of said measuring passage and smaller than the corresponding cross-sectional dimension of said outer cavity,
said cylindrical sleeve is formed with a first annular shoulder (61) which surrounds said mouth and adjoins and faces said constricted passage, and with a second annular shoulder, which faces and adjoins said outer cavity and constricted passage at its end which is remote from said mouth,
each of said electrode means comprises a body contained in said outer cavity and a projection (17) extending in said constricted passage and having an end face (18) bearing on said first shoulder (61) and adjoining said measuring passage (4), and
an elastic sealing ring (14) surrounds said projection (17) and is clamped between said second shoulder and said body.

11. In a measuring system, comprising
a base,
passage-defining means mounted on said base and defining a measuring passage having an entrance portion and an exit portion,
a plurality of ion-selective sensing electrodes adjoining said measuring passage between said entrance and exit portions and spaced apart along said measuring passage and adapted to examine fluid samples flowing through said measuring passage from said entrance portion to said exit portion and contacting said sensing electrodes, an inlet device connected to said entrance portion, and an outlet device connected to said exit portion, the improvement residing in that said measuring passage comprises a plurality of bends, each of which is adjoined by one of said sensing electrodes and has curved portions respectively preceding and succeeding said sensing electrode in the direction from said entrance portion to said exit portion, each of said sensing electrodes adjoins said bend on the outside thereof, and electrode-mounting means are provided and carry said sensing electrodes, wherein said passage-defining means comprise a measuring passage cylinder, which is mounted on said base and defines a measuring passage formed with a plurality of bends and a cylindrical sleeve, which surrounds said measuring passage cylinder and is formed with radial through openings, ion-selective sensing electrode means comprising said sensing electrodes extending in said openings, said ion-selective sensing electrodes are comprised in ion-selective sensing electrode means extending in said openings and adjoining said measuring passage, said inlet device and said outlet device extend through said cylindrical sleeve, and a shield is provided, which is removably mounted on said base and consists of an electrically conducting, closed cover acting as a protective screen.

12. In a measuring system comprising:

passage-defining means defining a measuring passage having an entrance portion and an exit portion, a plurality of ion-selective sensing electrodes adjoining said measuring passage between said entrance and exit portions and spaced apart along said measuring passage and adapted to examine fluid samples flowing through said measuring passage from said entrance portion to said exit portion and contacting said sensing electrodes, an inlet device connected to said entrance portion, and an outlet device connected to said exit portion, the improvement comprising that said measuring passage comprises a plurality of bends, each of which is adjoined by one of said sensing electrodes and has curved portions respectively preceding and succeeding said sensing electrode in the direction from said entrance portion to said exit portion, wherein each of said sensing electrodes adjoins said bend on the outside thereof, and electrode-mounting means are provided and carry said sensing electrodes, wherein said measuring passage extends along a rising helix, and said sensing electrodes are arranged on different levels.

13. In a measuring system comprising passage-defining means defining a measuring passage having an entrance portion and an exit portion, a plurality of ion-selective sensing electrodes adjoining said measuring passage between said entrance and exit portions and spaced apart along said measuring passage and adapted to examine fluid samples flowing through said measuring passage from said entrance portion to said exit portion and contacting said sensing electrodes, an inlet device connected to said entrance portion, and an outlet device connected to said exit portion, the improvement comprising that said measuring passage comprises a plurality of bends, each of which is adjoined by one of said sensing electrodes and has curved portions respectively preceding and succeeding said sensing electrode in the direction from said entrance portion to said exit portion, wherein each of said sensing electrodes adjoins said bend on the outside thereof, and electrode-mounting means are provided and carry said sensing electrodes, wherein said measuring passage comprises an intermediate portion connecting said entrance and exit portions and extending on a circular line, said entrance and exit portions are offset from said circular line, and said sensing electrodes constitute a star-shaped array.

14. The improvement set forth in claim 13, wherein a reference electrode (22) is provided, which adjoins said measuring passage (4) between said outlet device and one (21) of said sensing electrodes which is nearest to said outlet device.

15. The improvement set forth in claim 14, wherein said passage-defining means, said sensing electrodes and said reference electrode are comprised in a subassembly, an electrically conducting cover (33) is connected to said subassembly by a hinge (34), a housing component is provided and adapted to be covered by said cover, a rinsing liquid inlet device (40) is mounted on said housing component and contained in said cover and communicates with said measuring passage between said reference electrode (22) and said nearest sensing electrode (21), and a rinsing liquid port is provided on the outside of said cover and communicates with said rinsing liquid inlet device.

16. The improvement set forth in claim 13, wherein said sensing electrodes are provided with contacts (30, 31; 62, 64), said passage-defining means comprise a cylindrical component (3) defining said measuring passage and formed with a plurality of openings (6–9), each of which extends inwardly to and opens into one of said bends and is radial with respect to said bend, one of said sensing electrodes extends in each of said openings, said passage-defining means and said sensing electrodes are comprised in a subassembly, an electrically conducting cover (33) is connected to said subassembly by a hinge (34), at least one circular series of contact and contact pressure springs (28, 29) is provided, which series is concentric to said cylindrical component, said contact and contact pressure springs of said series are mounted on a ring, which is yieldably mounted in said cover (33) by additional springs, and the arrangement is such that said contact and contact springs engage said contacts of said sensing electrodes when said cover is closed on said subassembly.

17. In a measuring system comprising:

passage-defining means defining a measuring passage having an entrance portion and an exit portion, a plurality of ion-selective sensing electrodes adjoining said measuring passage between said entrance and exit portions and spaced apart along said measuring passage and adapted to examine fluid samples flowing through said measuring passage from said entrance portion to said exit portion and contacting said sensing electrodes, an inlet device connected to said entrance portion, and an outlet device connected to said exit portion, the improvement comprising that said measuring passage comprises a plurality of bends, each of which is adjoined by one of said sensing electrodes and has curved portions respectively preceding and succeeding said sensing electrode in the direction from said entrance portion to said exit portion, wherein each of said sensing electrodes adjoins said bend on the outside thereof, and electrode-mounting means are provided and carry said sensing electrodes, wherein said passage-defining means comprise a substantially circular housing member defining said measuring passage and formed with openings leading to respective ones of said bends, each of said sensing electrodes extends in one of said openings, latching springs carrying latching elements are provided in said housing member and are associated each with one of said openings and each extend parallel to the associated opening, each of said sensing electrodes is comprised in an electrode assembly formed with a detent recess receiving one of said latching elements, and each of said detent recesses is longer in the direction of said opening than the associated latching element.

18. In a measuring system comprising passage-defining means defining a measuring passage having an entrance portion and an exit portion, a plurality of ion-selective sensing electrodes adjoining said measuring passage between said entrance and exit portions and spaced apart along said measuring passage and adapted to examine fluid samples flowing through said measuring passage from said entrance portion to said exit portion and contacting said sensing electrodes, an inlet device connected to said entrance portion, and an outlet device connected to said exit portion, the improvement comprising that said measuring passage comprises a plurality of bends, each of which is adjoined by one of said sensing electrodes and has curved portions respectively preceding and succeeding said sensing electrode in the direction from said entrance portion to said exit portion, wherein each of said sensing electrodes adjoins said bend on the outside thereof, and electrode-mounting means are provided and carry said sensing electrodes, wherein a circular housing member is provided, said passage-defining means comprise a transparent measuring passage cylinder, which defines said measuring passage and is concentrically arranged in said housing member, said measuring passage extends along a circular line from said entrance portion to said exit portion, and said measuring passage cylinder is provided with a centrally disposed, open-topped recess for a visual inspection of said measuring passage.

19. The improvement set forth in claim 18, wherein said recess (5) is conical and flares upwardly and has side faces having an inclination of about 45°.

* * * * *